United States Patent
Nakada et al.

(10) Patent No.: US 8,647,498 B2
(45) Date of Patent: Feb. 11, 2014

(54) CORROSIVE ENVIRONMENT SENSOR AND METHOD FOR MEASURING CORROSIVE ENVIRONMENT

(75) Inventors: Ruri Nakada, Shizuoka (JP); Nobutoshi Konagai, Shizuoka (JP); Kota Sako, Shizuoka (JP); Yuya Ito, Shizuoka (JP)

(73) Assignee: Suzuki Motor Corporation, Shizuoka (JP)

( * ) Notice: Subject to any disclaimer, the term of this patent is extended or adjusted under 35 U.S.C. 154(b) by 52 days.

(21) Appl. No.: 13/431,153

(22) Filed: Mar. 27, 2012

(65) Prior Publication Data

US 2012/0261272 A1 Oct. 18, 2012

(30) Foreign Application Priority Data

Apr. 13, 2011 (JP) ................. 2011-089507

(51) Int. Cl.
*G01N 17/02* (2006.01)
(52) U.S. Cl.
USPC ...................... 205/775.5; 204/404
(58) Field of Classification Search
USPC ........................ 422/53; 204/404; 205/775.5
See application file for complete search history.

(56) References Cited

U.S. PATENT DOCUMENTS 5,865,971 A * 2/1999 Sunkara ................. 204/404
8,054,092 B2 * 11/2011 Fay et al. ................. 324/700

FOREIGN PATENT DOCUMENTS

GB 2244810 A * 12/1991 ............. G01N 27/30
JP 2005-134161 A 5/2005

OTHER PUBLICATIONS

Cčihal et al. "Trends in the Electrochemical Polarization Potentiodynamic Reactivation Method—EPR"—Chem. Biochem. Eng. Q 21 (1) 47-54 (2007).*
Prohaska et al. "On the substitution of conventional corrosion tests by an electrochemical potentiokinetic reactivation test," Corros. Sci. (2010).*
Product literature for Gamry Instruments DC105 ™ Corrosion Techniques Software (Sep. 8, 2010), four unnumbered pages.*
Mickaianis A Survey of Techniques for Corrosion Monitoring (U), Westinghouse Savannah River Company, WSRC-TR-92-472 (U), issued: Oct. 1992.*
Whitten et al., "Electrochemical Testing of Corrosion Inhibition for Galvanically Coupled Alloys," Northern Area Western Conference Calgary, Alberta, Feb. 6-9, 2006.*
JPO computer-generated English language translation of JP 2005-134161 A, downloaded Jun. 4, 2013.*

* cited by examiner

*Primary Examiner* — Alex Noguerola
(74) *Attorney, Agent, or Firm* — Troutman Sanders LLP

(57) ABSTRACT

A corrosive environment sensor for measuring corrosive environment inside a space between a first member that is a conductor and a second member that is a conductor or insulator includes: a base having a surface which cam face the first member that is a conductor; and an electrode which is provided on the surface of the base and formed with a material different in ionization tendency from the first member and which faces at a distance the first member so as to form a galvanic coupling with the first member, and the corrosive environment sensor measures a galvanic current between the electrode and the first member.

9 Claims, 5 Drawing Sheets

CORROSIVE ENVIRONMENT SENSOR AND METHOD FOR MEASURING CORROSIVE ENVIRONMENT

CROSS-REFERENCE TO RELATED APPLICATIONS

This application is based upon and claims the benefit of priority of the prior Japanese Patent Application No. 2011-089507, filed on Apr. 13, 2011, the entire contents of which are incorporated herein by reference.

BACKGROUND OF THE INVENTION

1. Field of the Invention

The present invention relates to corrosive environment sensors and methods for measuring corrosive environment. More specifically, the present invention relates to a corrosive environment sensor preferable for measuring the corrosive environment inside a space present in a structure and a method for measuring corrosive environment inside a space present in a structure with use of the corrosive environment sensor. The term "corrosive environment" herein refers to an influence of environment exerted on the corrosion of a structure and the like (i.e., corrosiveness of the environment).

2. Description of the Related Art

A structure constituted by combining metallic members may have spaces at portions where the metallic members overlap each other. For example, in the constitution where overlapping portions of metallic members are spot-welded, the metallic members may fail to have a tight contact with each other and thereby a space is generated therein. It has been found out that the inside of such a space is easy to corrode as compared with a portion open to the outside air. The reason thereof is considered as shown below. That is, moisture tends to enter into the inside of such a space and is hardly dried due to capillarity. Accordingly, the humidity inside the space is maintained high as compared with the outside air. To prevent corrosion of metallic members, a method for applying an anticorrosion paint may be used. However, since the anticorrosion paint is hard to sink into the inside of such a space, it may be impossible to sufficiently apply the anticorrosion paint to the inside of the space.

Vehicles such as automobiles also have the structure formed by combining metallic members. For example, the chassis and the body of an automobile are a structure constituted by welding metallic members to each other. When the automobile is driven in the rain and the snow, rainwater and moisture containing snow melting agents may adhere to the structure and enter into a space therein to cause corrosion. Accordingly, it is important for corrosion control design of the automobile structure to understand the corrosive environment of such a space.

As a corrosive environment sensor for measuring the corrosiveness of the environment in which a structure is used, there is known, for example, an ACM (Atmospheric Corrosion Monitor) sensor (hereinafter referred to as "ACM sensor"). The ACM sensor, which has two types of electrodes made of metals having different ionization tendencies, is constituted so that these two types of electrodes are insulated by an insulating material. When water comes into contact with both of these two types of electrodes due to rainfall and dew condensation, a galvanic current flows between the two types of electrodes. The galvanic current has a good correlation with a corrosion rate (i.e., corrosiveness of the environment). Accordingly, the corrosiveness of the environment can be monitored by measuring the galvanic current. In designing constructions such as bridges and residences, the galvanic current is continuously measured with the ACM sensor, and the measurement results are used for calculating life of respective parts of the structure and the like.

However, it is difficult to measure the corrosive environment inside a space present in the structure with use of the ACM sensor. When the electrodes of the ACM sensor come into contact with the structure, electric current may pass between the electrodes and the structure and also the electrodes may short-circuit to each other, which may hinder accurate measurement of the galvanic current. Since the size of the spaces present in the structure is generally small, it is difficult to place the ACM sensor inside minimal spaces without the electrodes coming into contact with the structure.

In the corrosion tests of structures and the like, a combined cyclic corrosion tester may be used. The combined cyclic corrosion tester can reproduce atmospheric corrosion. However, it is difficult to fully reproduce the environment. Moreover, the measurement results have large individual differences and variations.

In order to measure the corrosive environment inside a space between members, a constitution disclosed in Patent Document 1 may be considered for example. A corrosive environment sensor disclosed in Patent Document 1 has space formation members which face a detection section at a specified interval. The space formation members form a space (i.e., a pseudo space) which imitates the actual space formed between members. By placing such a sensor in the vicinity of the portion where members overlap each other in the structure, the corrosive environment of the portion can be measured.

However, the corrosive environment sensor disclosed in Patent Document 1 cannot be placed directly in the space of the portion where the members overlap each other. The portion where the members overlap each other and other portions distanced from that portion are different in factors influencing the corrosive environment and measurement results, such as orientations of the corrosive environment sensor, vibrations of the structure and air currents. It is not possible, therefore, to make the corrosive environment of a pseudo space formed in the corrosive environment sensor completely coincident with the actual corrosive environment of the portion where members overlap each other.

Patent Document 1: Japanese Laid-open Patent Publication No. 2005-134161

SUMMARY OF THE INVENTION

In view of the above situation, an object of the present invention is to provide a corrosive environment sensor and a method for measuring corrosive environment, which allow accurate measurement of the corrosive environment of a space generated in a portion where members overlap each other. More particularly, an object of the present invention is to provide a corrosive environment sensor and a method for measuring corrosive environment, which allow direct measurement of the corrosive environment of a space generated in a portion where members overlap each other.

In order to accomplish the above object, a corrosive environment sensor of the present invention is a corrosive environment sensor for measuring corrosive environment inside a space between two members, at least one member of the two members being a conductor, the corrosive environment sensor including: a base having a surface which can face the one member that is a conductor; and an electrode which is provided on the surface of the base and formed with a material different in ionization tendency from the one member that is a conductor and which faces the one member that is a conductor at a distance to form a galvanic coupling with the one member that is a conductor.

A spacer is provided on the base for keeping the one member that is a conductor at a distance from the electrode.

An engaging section for engaging with the other member of the two members is provided on the base.

A method for measuring corrosive environment in the present invention is a method for measuring corrosive environment in side a space between two members, at least one member of the two members being a conductor, the method, including the steps of: placing an electrode made of a material different in ionization tendency from the one member that is a conductor so that the electrode faces the one member at a distance; and measuring a galvanic current between the electrode and the one member that is a conductor.

A method for measuring corrosive environment in the present invention is a method for measuring corrosive environment inside a space between two members, at least one member of the two members being a conductor, the method including the steps of: forming a notch or opening in the other member which faces the one member that is a conductor; placing on the notch or opening formed in the other member a corrosive environment sensor having an electrode which is made of a material different in ionization tendency from the one member and which is provided on a surface of a base, so that the electrode faces the one member that is a conductor at a distance; and measuring a galvanic current between the electrode and the one member that is a conductor.

A distance between the electrode and the one member that is a conductor is equal to a distance between the one member that is a conductor and the other member.

A spacer in a projecting shape is provided on the base to maintain a state that the electrode is at a distance from the one member that is a conductor.

The notch or opening formed in the other member is closed with the base.

The base has a thickness similar to a thickness of the other member, and a flange-like engaging section is provided on the base, so that the engaging section engages with the other member to maintain that a distance between the electrode and the one member that is a conductor is equal to a distance between the one member that is a conductor and the other member.

The term "two members" stated in the present invention does not limitedly refer to two separate and independent members. For example, a space generated in an overlapping portion of one member generated by folding and the like also serves as a measuring object. It is only for the sake of explanation that a portion forming one inner surface of a space is referred to as "one member" while a portion forming the other inner surface of the space is referred to as "the other member."

According to the present invention, it becomes possible to accurately measure the corrosive environment of a space generated in a portion where members overlap each other. According to the present invention, it becomes possible to directly measure the corrosive environment of a space generated in a portion where members overlap each other in particular.

DETAILED DESCRIPTION OF THE PREFERRED EMBODIMENTS

Figure 1:
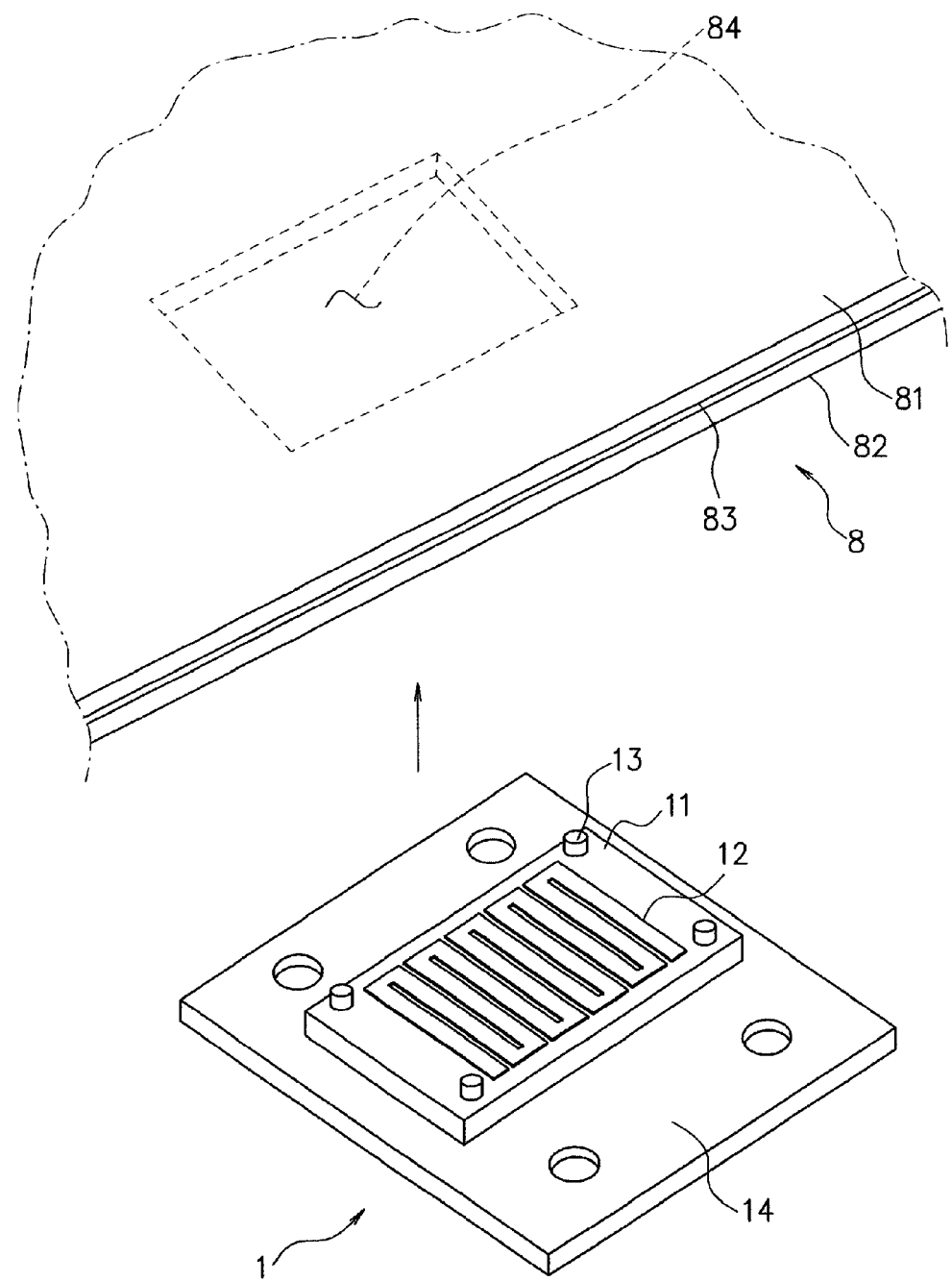
FIG. 1 is a perspective view for schematically showing the constitution of a corrosive environment sensor of the present invention and the constitution of the corrosive environment sensor mounted on a structure.
Figure 2:
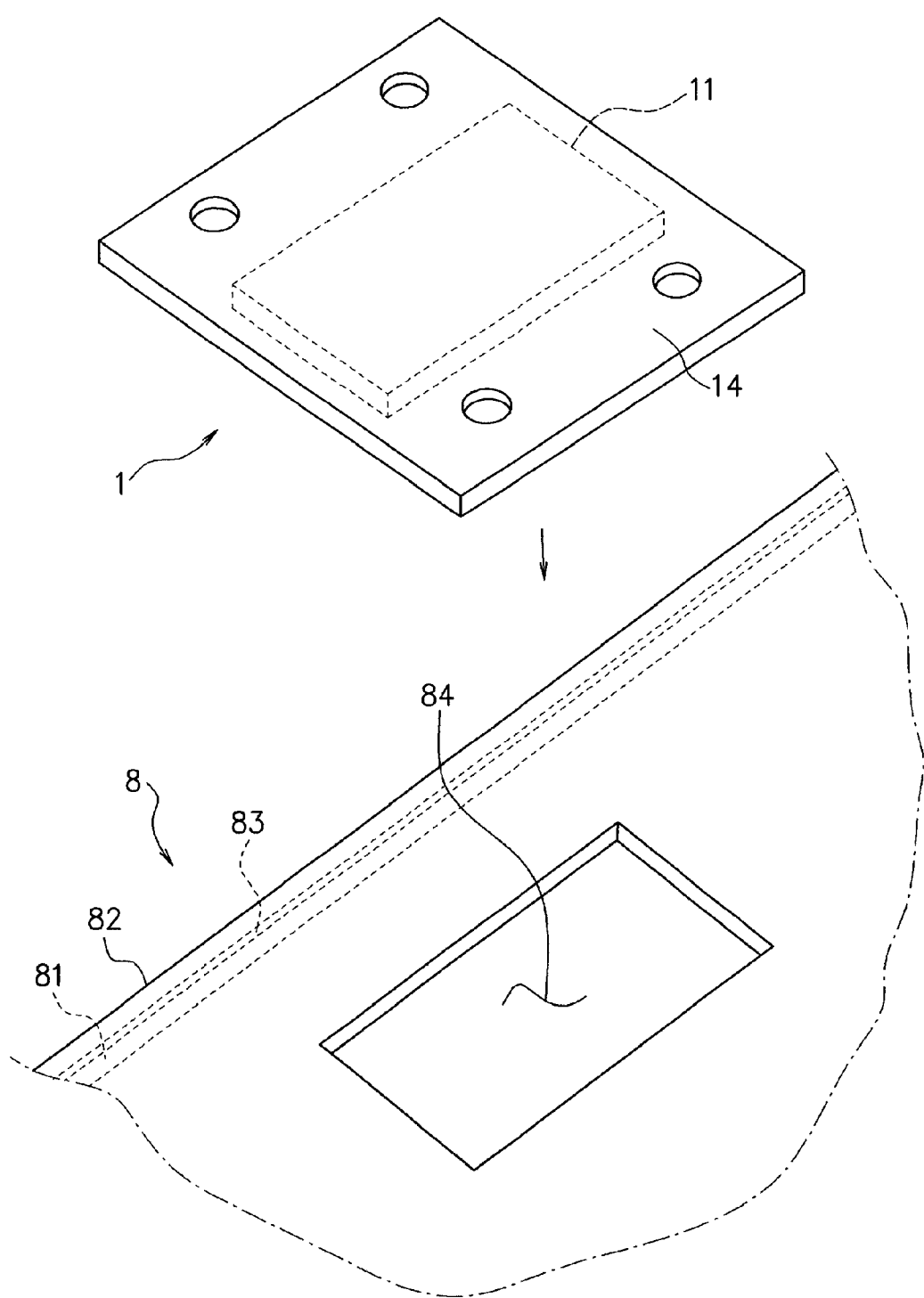
FIG. 2 is a perspective view for schematically showing the constitution of the corrosive environment sensor of the present invention and the constitution of the corrosive environment sensor mounted on a structure as seen from the opposite side of FIG. 1.
Figure 3:
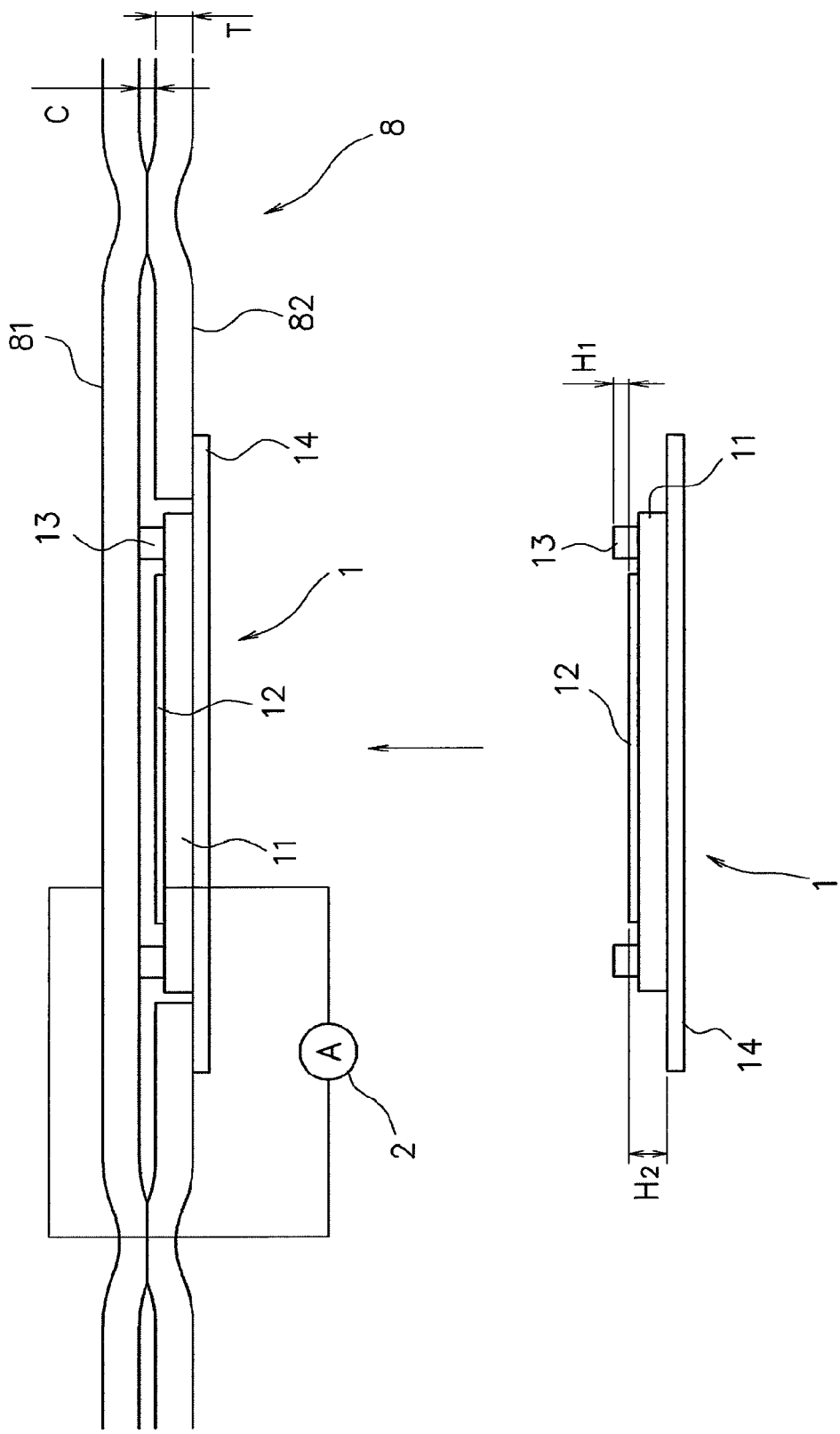
FIG. 3 is a cross sectional view for schematically showing the constitution of the corrosive environment sensor of the present invention and the constitution of the corrosive environment sensor mounted on a structure.

Hereinafter, the embodiment of the present invention will be described in detail with reference to the accompanying drawings. A corrosive environment sensor 1 according to the embodiment of the present invention can measure the corrosive environment of a space between two members, at least one member of the two members being a conductor. The term "corrosive environment" herein refers to an influence of environment exerted on the corrosion of a structure and the like (i.e., corrosiveness of the environment). In the following description, a measuring object is exemplified by a structure 8 having an overlapping section where a first member 81 and a second member 82 overlap. FIGS. 1 to 3 are extracted views of the overlapping section where the first member 81 and the second member 82 overlap. The first member 81 is a conductor. In the case where the first member 81 has no conduction, an insulating layer or film (e.g., a coating and oxide) on the surface of the first member 81 may be removed, or a foil (e.g., an iron foil) made of a conductor may be applied to the surface. As a result, the surface of the first member 81 may obtain electric conduction. It is to be noted that the second member 82 may be a conductor or an insulator. The first member 81 corresponds to "one member" of the present invention, while the second member 82 corresponds to "the other member" of the present invention.

A description will be first given of the constitution of the corrosive environment sensor 1 according to the embodiment of the present invention with reference to FIGS. 1 to 3. For the sake of explanation, the corrosive environment sensor 1 according to the embodiment of the present invention may be referred to as "the corrosive environment sensor 1 of the present invention." FIGS. 1 to 3 are views for schematically showing the constitution of the corrosive environment sensor 1 of the present invention and the constitution of the corrosive environment sensor 1 mounted to the overlapping section of the structure 8. FIG. 1 and FIG. 2 are perspective views, each seen from the opposite side of each other, and FIG. 3 is a cross sectional view. As shown in FIGS. 1 to 3, the corrosive environment sensor 1 of the present invention includes a base 11, an electrode 12, a spacer 13 and an engaging section 14.

The base 11 is a plate-like portion having a specified thickness and electric insulation. The base 11 also has a function of closing a notch or opening 84 formed in the second member 82 of the structure 8. One surface in the thickness direction of the base 11 is the surface which can face the first member 81 of the structure 8. Although the base 11 is formed to have a planar constitution in FIGS. 1 to 3, the base 11 is not limited to this planar constitution. The shape of the base 11 is set according to the shape of an overlapping section of the first member 81 and the second member 82 in the structure 8. For example, when the overlapping section of the first member 81 and the second member 82 is formed into the shape of a curved surface, the base 11 is formed after the overlapping section of the first member 81 and the second member 82 into the curved surface shape.

The electrode 12 is formed on one surface in the thickness direction of the base 11 (the surface which can face the first member 81 in this case). For example, the electrode 12 has a plate-like or film-like constitution, and is fixed by bonding and the like to one surface in the thickness direction of the base 11. In the state where the corrosive environment sensor 1 of the present invention is fixed to the structure 8, the electrode 12 faces, at a distance, a surface of the first member 81 that is a conductor on the inner side of a space 83, and thereby forms a galvanic coupling with the first member 81. The electrode 12 is an electric conductor formed with a material different in ionization tendency from the first member 81. Particularly, the electrode 12 should preferably be constituted from a material smaller in ionization tendency (i.e., an electropositive material) than the first member 81. For example, when the first member 81 is made of an iron-based material (e.g., iron and steel), or made of a galvanized steel sheet, silver and platinum can be used as the material of the electrode 12. The shape of the electrode 12 is not particularly limited. For example, the electrode 12 may have a simple plate-like shape, or the electrode 12 may have a mesh-like, grid-like or belt-like shape.

The spacer 13 is a structure to maintain the state where the electrode 12 is at a distance from the surface of the first member 81. For example, the spacer 13 is an insulator having a projecting or pillar-shaped structure and provided on the surface of the base 11 where the electrode 12 is provided. As shown in FIG. 3, a size $H_1$ from the surface of the electrode 12 to the top end of the spacer 13 is set equal to a size C of the space 83 between the first member 81 and the second member 82. It is to be noted that the spacer 13 may be constituted so as to be integrally formed with the base 11, or may be constituted so that the spacer 13 as a separate member is fixed to the base 11.

The engaging section 14 is a portion which can engage with a surface of the second member 82 on the outer side of the space 83 and which is an insulator. For example, the engaging section 14 has a rib-like or flange-like constitution which is provided on a periphery of the other surface in the thickness direction of the base 11 (the surface opposite to the surface where the electrode 12 and the spacer 13 are provided in this case) and which extends toward the outside in the plane direction of the base 11. When the engaging section 14 engages with the second member 82, the corrosive environment sensor 1 is positioned on the first member 81. It is to be noted that the engaging section 14 may be a member independent of the base 11, or may be constituted integrally with the base 11. As shown in FIG. 3, a size $H_2$ from the surface of the engaging section 14 to the surface of the electrode 12 is set generally equal to a thickness T of the second member 82. Adjustment of the size $H_2$ is implemented with the base 11.

A description is now given of a mounting constitution (mounting method) of the corrosive environment sensor 1 to the structure 8 and a method for measuring corrosive environment of the space 83 in the structure 8 with use of the corrosive environment sensor 1 of the present invention.

The mounting constitution (mounting method) of the corrosive environment sensor 1 to the structure 8 is as shown below. First, in an overlapping section of the first member 81 and the second member 82 in the structure 8, the notch or opening 84 is formed in the second member 82. Alternatively, an overlapping section is formed from the first member 81 and the second member 82 having the notch or opening 84 previously formed therein. While the base 11 of the corrosive environment sensor 1 can be inserted into the notch or opening 84, the engaging section 14 is dimensioned and shaped so as not to be inserted therein. For example, the notch or opening 84 is dimensioned and shaped generally identical to the base 11 or slightly larger than the base 11. Upon formation of the notch or opening 84 in the second member 82, the surface of the first member 81 on the inner side of the space 83 is exposed through the notch or opening 84. The base 11 of the corrosive environment sensor 1 is then inserted into the notch or opening 84. As a result, the engaging section 14 of the corrosive environment sensor 1 comes into contact with the surface of the second member 82 on the outer side of the space 83. Consequently, one surface of the base 11 and the electrode 12 of the corrosive environment sensor 1 face the surface of the first member 81 on the inner side of the space 83. In the state where the engaging section 14 is in contact with the surface of the second member 82 on the outer side of the space 83, the corrosive environment sensor 1 is fixed to the structure 8. For example, the engaging section 14 is screwed to the second member 82 through a through hole formed in the engaging section 14. The electrode 12 and the first member 81 are then connected to an ammeter 2 (see FIG. 3). The ammeter 2 can measure a current (i.e., galvanic current) which flows between the electrode 12 and the first member 81.

As shown in FIG. 3 in particular, the size $H_2$ from the engaging section 14 to the surface of the electrode 12 is set equal to the thickness T of the second member 82. Further, the size $H_1$ between the surface of the electrode 12 and the top end of the spacer 13 is set equal to the size C of the space 83 between the first member 81 and the second member 82. Accordingly, with the corrosive environment sensor 1 of the present invention mounted to the structure 8, a distance between the surface of the electrode 12 and the surface of the first member 81 on the inner side of the space 83 is equal to the size C of the space 83 between the first member 81 and the second member 82. The spacer 13 maintains the state where the electrode 12 is away from the first member 81 by the above distance. Therefore, the electrode 12 made of a material different in ionization tendency from the first member 81 is placed so that the electrode 12 faces the first member 81 at a distance. The base 11 and the engaging section 14 close the notch or opening 84 formed in the second member 82. Accordingly, the environment of a space where the first member 81 faces the corrosive environment sensor 1 is maintained similar to the environment of the space 83 between the first member 81 and the second member 82 (the portion other than the notch or opening 84).

When moisture enters in between the corrosive environment sensor 1 and the first member 81 and comes into contact with both the electrode 12 and the first member 81, the electrode 12 and the first member 81 form a galvanic coupling and thereby a galvanic current flows therebetween. The galvanic current has a good correlation with a corrosion rate of the members constituting the galvanic coupling. Accordingly, the corrosive environment of the space 83 can be measured by measuring the current (galvanic current) generated between the electrode 12 and the first member 81 with the ammeter 2. Thus, the corrosive environment sensor 1 of the present invention uses the first member 81, which constitutes the inner surface of the space 83 that is a measuring object, as an electrode for measuring the galvanic current. According to such constitution, the corrosive environment sensor 1 of the present invention can be placed inside the space 83 between the first member 81 and the second member 82. This makes it possible to directly measure the corrosive environment inside the space 83. The notch or opening 84 formed in the second member 82 is closed by the base 11 and the engaging section 14. Further, the distance between the electrode 12 and the first member 81 is maintained equal to the size C of the space 83. Accordingly, the corrosive environment of a portion where the corrosive environment sensor 1 is provided is maintained similar to the state of the space 83 in the overlapping section between the first member 81 and the second member 82. This makes it possible to accurately measure the corrosive environment of the space 83. Since the spacer 13 is provided on the surface of the base 11, the electrode 12 and the first member 81 are maintained in the state of being at a distance from each other and therefore do not come into contact with each other even when the structure 8 vibrates. Therefore, it becomes possible to mount the corrosive environment, sensor 1 on automobiles and the like and to measure the corrosive environment during actual driving.

Working Example

Figure 4:
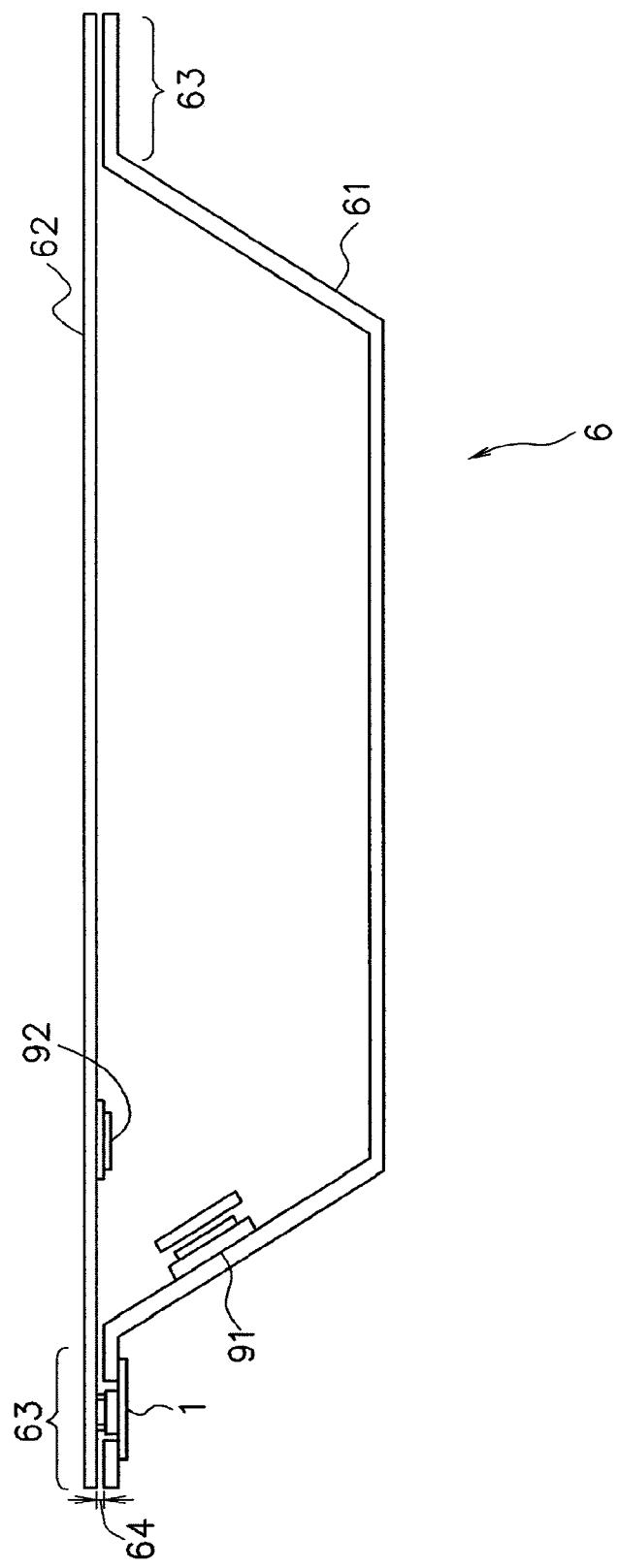
FIG. 4 is a cross sectional view for schematically showing the mounting configuration of the corrosive environment sensor of the present invention and conventional corrosive environment sensors.
Figure 5:
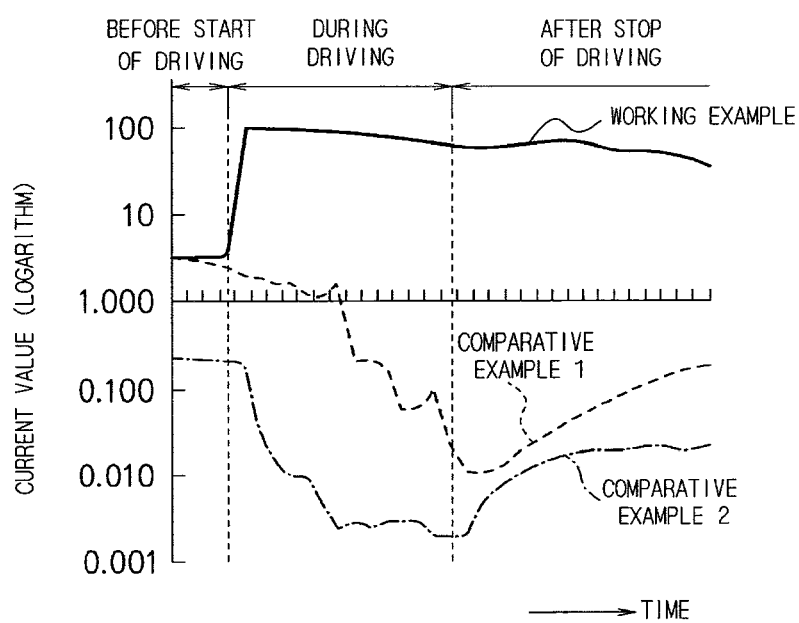
FIG. 5 is a graph view showing measurement results of galvanic current with use of the corrosive environment sensor of the present invention and the conventional corrosive environment sensors.

A description is now given of a measurement example (working example) of the corrosive environment with use of the corrosive environment sensor 1 of the present invention in comparison to measurement examples (comparative examples 1 and 2) of the corrosive environment with use of conventional corrosive environment sensors 91 and 92 with reference to FIG. 4 and FIG. 5. The corrosive environment sensor 1 and the conventional corrosive environment sensors 91 and 92 were attached to a front member 6 of an automobile, and the automobile was driven in the rain to measure a galvanic current. FIG. 4 is a cross sectional view for schematically showing the mounting configuration of the corrosive environment sensor 1 and the conventional corrosive environment sensors 91 and 92 to the front member 6. FIG. 5 is a graph view showing measurement results of galvanic current with use of the corrosive environment sensor 1 and the conventional corrosive environment sensors 91 and 92. One conventional corrosive environment sensor 91 is referred to as "corrosive environment sensor 91 in the comparative example 1", while the other conventional corrosive environment sensor 92 is referred to as "corrosive environment sensor 92 in the comparative example 2."

The mounting configuration of the corrosive environment sensor 1 of the present invention and the corrosive environment sensors 91 and 92 in the comparative examples 1 and 2 will be described with reference to FIG. 4. The front member 6 of an automobile, which is a mounting destination of the sensor, is a structure whose inside is a shell-shaped hollow and which is constituted of a plurality of press-molded and spot-welded metallic members. More specifically, the front member 6 has an overlapping section 63 where two metallic members 61 and 62 overlap each other. In the overlapping section 63, the two metallic members 61 and 62 are spot-welded. Accordingly, in the overlapping section 63, a space 64 is generated between the two metallic members 61 and 62. An opening is formed in one of the two metallic members 61 and 62 (the metallic member 61 in this case), and the corrosive environment sensor 1 is mounted to the opening. The corrosive environment sensor 91 in the comparative example 1 has space formation members, and an electrode is provided inside a space formed with the space formation members. The corrosive environment sensor 92 in the comparative example 2 does not have the space formation members, so that an electrode thereof is exposed to the outside air. Since the corrosive environment sensors 91 and 92 in these comparative examples 1 and 2 cannot be mounted inside the space 64 between the two metallic members 61 and 62, the corrosive environment sensors 91 and 92 are mounted in the vicinity of the overlapping section 63 of the two metallic members 61 and 62 inside the front member 6.

Measurement results of the galvanic current with the corrosive environment sensor 1 of the present invention and with the corrosive environment sensors 91 and 92 in the comparative examples 1 and 2 will be described with reference to FIG. 5. As shown in FIG. 5, before the start of driving, a current value of the corrosive environment sensor 1 (working example) and a current value of the corrosive environment sensor 91 in the comparative example 1 are larger than a current value of the corrosive environment sensor 92 in the comparative example 2. The inside of the space 64 between the two metallic members 61 and 62 in which the corrosive environment sensor 1 is mounted and the inside of a pseudo space formed with the corrosive environment sensor 91 in the comparative example 1 tend to collect moisture as compared with a portion open to the outside air. The above measurement results are considered to be attributed to this tendency. Therefore, the corrosive environment sensor 1 of the present invention can accurately measure the corrosive environment of the space 64 between the two metallic members 61 and 62 before the start of driving. It can be considered that the space formation members of the corrosive environment sensor 91 in the comparative example 1 reproduce the corrosive environment of the space 64 between the two metallic members 61 and 62 before the start of driving. It can be considered that as compared with the corrosive environment sensor 91, the corrosive environment sensor 92 in the comparative example 2 cannot accurately measure the corrosive environment of the space 64.

After the start of driving (during driving), the current value of the corrosive environment sensor 1 (working example) rapidly increases and then a generally constant value is maintained. This is considered to be because moisture enters into the space 64 when the automobile starts driving in the rain, and the humidity inside the space 64 is maintained high. As compared with the working example, the current values of the corrosive environment sensors 91 and 92 in the comparative examples 1 and 2 decrease after the start of driving. This is considered to be because a water film on the electrodes of the corrosive environment sensors 91 and 92 in the comparative examples 1 and 2 is evaporated by the air flow generated by the driving. Particularly, the current value in the corrosive environment sensor 91 in the comparative example 1 falls gradually whereas the current value of the corrosive environment sensor 92 in the comparative example 2 rapidly falls after the start of driving. This is considered to be because the corrosive environment sensor 91 in the comparative example 1 has the space formation members so that the atmosphere around the electrode gradually dries, whereas the electrode of the corrosive environment sensor 92 in the comparative example 2 is open to the air so that the atmosphere around the electrode rapidly dries. Thus, even after the start of driving (during driving), the space 64 is maintained in a highly moist state as compared with other portions. Further, the current value of the corrosive environment sensor 1 (working example) accurately reflects the environment inside the space 64. In contrast to this, the current values of the corrosive environment sensors 91 and 92 in the comparative examples 1 and 2 do not accurately reflect the environment inside the space 64. Therefore, the corrosive environment sensor 1 of the present invention can accurately measure the corrosive environment of the space 64 between the two metallic members 61 and 62 during driving of the automobile. In contrast to the working example, the corrosive environment sensors 91 and 92 in the comparative examples 1 and 2 cannot perform accurate measurement.

After the stop of driving, the current value of the corrosive environment sensor 1 (working example) falls gradually. This is considered to be because the stop of driving stops the moisture from entering into the space 64, so that the inside of the space 64 gradually dries. As compared with the working example, the current values of the corrosive environment sensors 91 and 92 in the comparative examples 1 and 2 gradually increase. This is considered to be because the humidity gradually increases due to lack of running wind. Thus, it can be considered that the current value of the corrosive environment sensor 1 (working example) accurately reflects the inside state of the space 64 after the stop of driving of the automobile. Accordingly, the corrosive environment sensor 1 can accurately measure the corrosive environment inside the space 64 after the stop of driving of the automobile. As compared with the working example, the corrosive environment sensors 91 and 92 in the comparative examples 1 and 2 can not accurately measure the corrosive environment inside the space 64 after the stop of driving of the automobile.

As described above, the corrosive environment sensor 1 can accurately measure the corrosive environment inside the space 64 between the two metallic members 61 and 62 in all the points including before the start of driving, during driving and after the stop of driving of the automobile. As compared with the working example, the corrosive environment sensors 91 and 92 in the comparative examples 1 and 2 are influenced by the air flow generated by driving, which hinder accurate measurement of the corrosive environment inside the space 64. Particularly in the corrosive environment sensor 92 in the comparative example 2, the electrode is open to the air and is largely influenced by running wind. The corrosive environment sensor 91 in the comparative example 1 has the space formation members and can accurately reproduce the corrosive environment of the space 64 before the start of driving. However, the corrosive environment sensor 91 cannot provide accurate measurement after the start of driving (during driving) and after the stop of driving.

Although the embodiment (working example) of the present invention has been described in detail as above, the embodiment (working example) is to be considered only as a concrete example of implementing the present invention. The technical scope of the present invention is not to be construed in a restrictive manner by the embodiment (working example) disclosed. That is, the present invention may be embodied in a number of different ways without departing from the technical scope or main features thereof. For example, in the embodiment disclosed, the base had a plate-like constitution, though the base may have a block-like constitution instead. The size and shape of the base are set according to the size and shape of the members constituting a structure.

The term "two members" stated in the present invention does not limitedly refer to "two separate and independent members". For example, a space generated in an overlapping port ion of one member formed by folding and the like also serves as a measuring object. It is only for the sake of explanation that a portion forming one inner surface of a space is referred to as "one member" while a portion forming the other inner surface of the space is referred to as "the other member."

The present invention relates to a corrosive environment sensor and a method for measuring corrosive environment. According to the present invention, it becomes possible to accurately measure the corrosive environment of a space generated in a portion where members overlap each other.

According to the present invention, it becomes possible to directly measure the corrosive environment of a space generated in a portion where members overlap each other in particular.

What is claimed is:

1. A corrosive environment sensor for measuring corrosive environment inside a space between two members, at least one member of the two members being a conductor, the corrosive environment sensor comprising:
    a base having a surface which can face the one member that is a conductor; and
    an electrode which is provided on the surface of the base and formed with a material different in ionization tendency from the one member that is a conductor and which faces the one member that is a conductor at a distance to have a space between the electrode and the one member,
    wherein the electrode forms a galvanic coupling with the one member that is a conductor by an electrolyte that intrudes into the space.

2. The corrosive environment sensor according to claim 1, wherein a spacer is provided on the base for keeping the one member that is a conductor at a distance from the electrode and a dimension from a surface of the electrode to a tip of the spacer is substantially the same as that of a space between the two members.

3. The corrosive environment sensor according to claim 1, wherein an engaging section for engaging with the other member of the two members is provided on the base and a dimension from a surface of the engaging section to a surface of the electrode is substantially the same as a thickness of the other member.

4. A method for measuring corrosive environment inside a space between two members, at least one member of the two members being a conductor, the method comprising the steps of:
    placing an electrode made of a material different in ionization tendency from the one member that is a conductor so that the electrode faces the one member at a distance to have a space between the electrode and the one member;
    forming a galvanic coupling by the electrode and the one member that is a conductor by an electrolyte that intrudes between the electrode and the one member that is a conductor; and
    measuring a galvanic current between the electrode and the one member.

5. A method for measuring corrosive environment inside a space between two members, at least one member of the two members being a conductor, the method comprising the steps of:
    forming a notch or opening in the other member which faces the one member that is a conductor;
    placing on the notch or opening formed in the other member a corrosive environment sensor having an electrode which is made of a material different in ionization tendency from the one member and which is provided on a surface of a base, so that the electrode faces the one member that is a conductor at a distance; and
    measuring a galvanic current between the electrode and the one member that is a conductor.

6. The method for measuring corrosive environment according to claim 5, wherein a distance between the electrode and the one member that is a conductor is equal to a distance between the one member that is a conductor and the other member.

7. The method for measuring corrosive environment according to claim 6, wherein a spacer in a projecting shape is provided on the base to maintain a state that the electrode is at a distance from the one member that is a conductor.

8. The method for measuring corrosive environment according to claim 5, wherein the notch or opening formed in the other member is closed with the base.

9. The method for measuring corrosive environment according to claim 5, wherein the base has a thickness similar to a thickness of the other member, and a flange-like engaging section is provided on the base so that the engaging section engages with the other member to maintain that a distance between the electrode and the one member that is a conductor is equal to a distance between the one member that is a conductor and the other member.

* * * * *